(12) United States Patent
Tang et al.

(10) Patent No.: US 9,475,768 B2
(45) Date of Patent: Oct. 25, 2016

(54) LUMINOGEN COMPOUNDS AND THE USE OF THE SAME FOR BIOSENSING AND CELLULAR IMAGING

(75) Inventors: Benzhong Tang, Hong Kong (CN); Yang Liu, Hong Kong (CN); Wing Yip Lam, Hong Kong (CN); Yong Yu, Hong Kong (CN)

(73) Assignee: THE HONG KONG UNIVERSITY OF SCIENCE AND TECHNOLOGY, Hong Kong (CN)

( * ) Notice: Subject to any disclaimer, the term of this patent is extended or adjusted under 35 U.S.C. 154(b) by 0 days.

(21) Appl. No.: 13/422,374

(22) Filed: Mar. 16, 2012

(65) Prior Publication Data

US 2012/0237964 A1   Sep. 20, 2012

Related U.S. Application Data

(60) Provisional application No. 61/457,393, filed on Mar. 17, 2011.

(51) Int. Cl.
| | | |
|---|---|---|
| *C07D 207/448* | (2006.01) | |
| *C09B 57/00* | (2006.01) | |
| *C07D 207/444* | (2006.01) | |
| *C09B 69/00* | (2006.01) | |

(52) U.S. Cl.
CPC ....... *C07D 207/444* (2013.01); *C07D 207/448* (2013.01); *C09B 57/00* (2013.01); *C09B 69/008* (2013.01); *Y10T 436/182* (2015.01)

(58) Field of Classification Search
None
See application file for complete search history.

(56) References Cited

U.S. PATENT DOCUMENTS 3,891,669 A * 6/1975 Kanaoka et al. ............ 548/525
6,020,206 A    2/2000 Vargeese et al.

2008/0220407 A1 * 9/2008 Tang .................. G01N 21/6428
                                                                    435/4
2010/0190658 A1   7/2010 Van Der Eycken et al.
2013/0089889 A1   4/2013 Tang et al.
2013/0266953 A1  10/2013 Tang et al.
2014/0255696 A1   9/2014 Tang et al.

FOREIGN PATENT DOCUMENTS

| JP | 61003066 A | 1/1986 |
|---|---|---|
| JP | 61110036 A | 5/1986 |
| JP | 2008185364 A | 8/2008 |

OTHER PUBLICATIONS

Hong et al., Chem. Commun., 2009, 4332-4353.*
Liu et al., Chem. Eur. J., 2010, 16, pp. 8433-8438.*
Jorge O. Escobedo, Oleksandr Rusin, Weihua Wang, Onur Alpturk, Kyu Kwang Kim, Xiangyang Xu, Robert M. Strongin, Detection of Biological Thiols, 139-162.
Phani Kumar Pullela, Taurai Chiku, Michael J. Carvan III, Daniel S. Sem, Fluorescence-based detection of thiols in vitro and in vivo using dithiol probes, Analytical Biochemistry, 2006, 352, 265-273.
Long Yi, Heyang Li, Lu Sun, Liangliang Liu, Cihong Zhang, Zhen Xi, A Highly Sensitive Fluorescence Probe for Fast Thiol-Quantification Assay of Glutathione Reductase, Communications: Fluorescent Probes, Angew. Chem. Int. Ed., 2009, 48, 4034-4037.

* cited by examiner

*Primary Examiner* — Alicia L Otton
(74) *Attorney, Agent, or Firm* — Nath, Goldberg & Meyer; Joshua B. Goldberg; Scott H. Blackman (57) ABSTRACT

Provided herein are a luminogen compound of formula (I) including a AIE luminophore moiety conjugated with a maleimide moiety and a use of the same for detecting thiol groups in biomolecules. Also provided is a dye molecule, a biosensor or a bioprobe comprising the luminogen compound of formula (I) in use for detecting thiol groups in biomolecules. The detection method of the present subject matter not only has high thio-selectivity and sensitivity, but also is rapid, convenient and handy.

14 Claims, 8 Drawing Sheets

LUMINOGEN COMPOUNDS AND THE USE OF THE SAME FOR BIOSENSING AND CELLULAR IMAGING

FIELD OF THE INVENTION

The present subject matter relates to a series of conjugated luminogen compounds and the use of the same for biosensing target molecules. In particular, the present subject matter relates to the conjugated luminogen compounds comprising an aggregation-induced emission (AIE) luminophore moiety and a maleimide moiety and the use of the same as a bioprobe or biosensor for detecting a thiol group in biomolecules.

BACKGROUND OF THE INVENTION

Cellular thiols are essential biomolecules that play important roles in biological systems as key components of protein structures and metabolic intermediates. The thiol molecules are critical in maintaining appropriate oxidation-reduction states of the proteins, cells and organisms. Glutathione (GSH), for example, is a thiol with the highest abundance in the cellular system. It is a small protein with a short sequence of Gly-Cys-Glu or GCE that resides in every cell of our body and is thus vital to life. Its deficiency results in cellular dysfunction. Many health problems, such as Alzheimer's disease, leucocyte loss, liver damage, psoriasis, cancer and AIDS are known to be associated with levels of cellular thiols.

The development of fluorescent probes for biomolecular detection has emerged as an active area of research due to its importance to bioscience and applications in biotechnology as well as its impact on public health. The fluorescent assay process offers a number of advantages over other analytical techniques, such as rapid response, high sensitivity, low background noise, and wide dynamic working range. Thanks to the enthusiastic effort of scientists devoted to this area of research, a large variety of fluorescent bioprobes have been developed. However, many of the bioprobes work in a "turn off" mode. For example, the emission of a fluorophore is switched "off" when it interacts with a quenching species in a biological system through a mechanism of fluorescence resonance energy transfer.

A sensitive and selective assay of thiols is thus of great biological implications. Much work has been done in the area of developing fluorescent sensors for thiol detection. In almost all the current sensing systems, thiols have been assayed by measuring the changes in the fluorescence signals of the probes with the analyte concentrations in the solution state using a spectrofluorometer. For real-world applications, however, it is preferable to perform the bioassays on solid strips because it requires no complex and expensive equipment and is thus simple, quick and convenient. No report has been found in the art about a thiol assay in the solid state to date.

A thorny problem often encountered by traditional fluorophores is aggregation-caused quenching (ACQ) of their emissions in the solid state. When dispersed in aqueous media or bound to biomolecules, the fluorophore molecules are inclined to aggregate, which usually quenches their fluorescence processes and thus greatly limits their effective ranges as bioprobes. The ACQ effect also makes it difficult to assay low-abundance molecular species in biological systems, because the fluorescence signals from the miniature amounts of the fluorophores matching the bioanalyte levels may be too weak to be determined accurately, while at the high fluorophore concentrations, the emissions are further weakened, rather than enhanced, due to the notorious ACQ effect.

An extraordinary phenomenon of aggregation-induced emission (AIE) that is exactly opposite to the ACQ effect discussed above, has been recently discovered. A series of fluorogen molecules that are non-emissive in solutions, such as tetraphenylethylene (TPE), are induced to emit efficiently by aggregate formation. The unique AIE effect has been utilized to develop new bioprobes of "turn on" type, which enjoy much higher sensitivity over their "turn off" counterparts. The selectivity of the AIE probes, however, is low and needs to be improved.

Accordingly, a new bioprobe with high selectivity while keeping its superb sensitivity has been desired in the art.

SUMMARY OF THE INVENTION

The aggregate-induced emission (AIE) luminogen compounds with high selectivity while maintaining high sensitivity have been found and are discussed herein, particularly the TPE-based AIE-active fluorogens. These compounds can be used to prepare a solid strip for thiol-specific detection in a sample containing small and big biomolecules, ranging from amino acids to proteins and to living cells. The compounds can be used as bioprobes or biosensosr for rapid, sensitive and selective detection of thiols in a sample.

Accordingly, the present subject matter, in one aspect, provides the conjugated luminogen compounds comprising an AIE luminophore moiety and a maleimide moiety, represented by the formula (I), below, wherein R is an aggregation-induced emission (AIE) luminophore. The AIE luminophore moiety of R and the maleimide moiety are conjugated together to form the compound of formula (I):

In another aspect, the present subject matter provides a method of detecting the presence or absence of a thiol group(s) in a sample comprising contacting the luminogen compound of formula (I) with the sample, particularly the target compound comprising a thiol(s) contained in the sample and detecting fluorescence. The change of fluorescence intensity is detected using, e.g., a UV-illumination reader. In this regard, the luminogen compounds can be used for imaging cellular thiols. In an embodiment, the method may comprise heating the test holders or strips containing the luminogen compounds of formula (I) and a solvent to accelerate evaporation of the solvent. In one embodiment, the sample may be a biological sample (or biosample), including a biological tissue or a biological fluid. In another embodiment, the luminogen compounds of formula (I) are contacted with free-thiol containing compounds in the sample.

Still in another aspect, the present subject matter provides the dye molecules, bioprobes or biosensors comprising the luminogen compounds of formula (I) as the detecting molecules. The biosensors may comprise a holder, such as a solid state medium, including a TLC (thin layer chromatography) plate or a paper-based medium. In one embodiment, the detecting molecules in the biosensors are held in place by the holder and are accessible to the target molecules or substances.

Still in another aspect, the present subject matter provides a kit for detecting the presence or absence of a thiol(s) in a sample comprising: a holder and a detecting agent comprising the luminogen compounds of formula (I), the detecting agent being held in place by the holder and being accessible to the target molecules or substances, a means for contacting the detecting agent with the sample, and a means for detecting fluorescence.

DETAILED DESCRIPTION OF THE INVENTION

Definitions

The following definitions are provided for the purpose of understanding the present subject matter and for constructing the appended patent claims.

It is noted that, as used in this specification and the appended claims, the singular forms "a," "an" and "the" include plural references unless the context clearly dictates otherwise.

"Sample" as used herein refers to anything which may contain a thiol group(s) for which detection or an assay is desired. The sample may be a solution of an amino acid, small protein, or oligopeptide. The sample may be a biological sample, such as a biological fluid from a host, for example, urine, blood, plasma, serum, saliva, semen, stool, sputum, cerebral spinal fluid, tears, mucus, amniotic fluid or the like. The biological sample may also be a biological tissue. Biological tissue refers to an aggregate of cells, usually of a particular kind together with their intercellular substance that forms one of the structural materials of a human, animal, plant, bacterial, fungal or viral structure, including connective tissue, epithelium, muscle tissue, and nerve tissues. Examples of biological tissues include organs, tumors, lymph nodes, arteries and individual cells.

"Analyte" or "Bioanylate" as used herein refers to the (bio) compound or composition to be detected.

"Detecting agent" as used herein refers to a compound which will react with a specific functional group that is present on species present in the sample, including a thiol group(s). In one embodiment, the detecting agent is a thiol-detecting agent. In one embodiment, the detecting agent is placed on a solid medium.

"Solid state medium" as used herein refers to a material that may have a shape of, e.g., strip, rod, particle, including beads and the like. In one embodiment, the solid medium is a TLC (Thin Liquid Chromatography) plate.

"Alkyl" refers to, unless otherwise specified, an aliphatic hydrocarbon group which may be a straight or branched chain. The alkyl may comprise about 1 to 15 carbon atoms in the chain, optionally substituted by one or more groups.

"Heteroaryl" as a group or part of a group refers to an optionally substituted aromatic monocyclic or multicyclic organic moiety. The heteroaryl may comprise about 5 to 10 ring members in which at least one ring member is a heteroatom. The heteroatom refers to an atom selected from the group consisting of nitrogen, oxygen, sulfur, phosphorus, boron and silicon.

"Cycloalkyl" refers to an optionally substituted non-aromatic monocyclic or multicyclic ring system. The cycloalkyl may comprise about 3 to 10 carbon atoms.

"Heterocycloalkyl" refers to a cycloalkyl group in which at least one ring member is a heteroatom. The heterocycloalkyl may comprise about 3 to 7 ring members.

"Aryl" as a group or part of a group refers to an optionally substituted monocyclic or multicyclic aromatic carbocyclic moiety, such as phenyl, naphthyl, anthracene, tetracene, pyrene, etc. The aryl may comprise about 6 to 18 carbon atoms.

"Heteroalkyl" refer to an alkyl in which at least one carbon atom is replaced by a heteroatom.

"Vinyl" refers to the presence of a pendant vinyl group ($CH_2=CH-$) in the structure of the molecules or the material described herein.

"Acetyl" refers to the presence of a pendant acetyl group ($COCH_3$) in the structure of the molecules or the material described herein.

Unless defined otherwise all technical and scientific terms used herein have the same meaning as commonly understood to one of ordinary skill in the art to which the presently described subject matter pertains.

Throughout the application, descriptions of various embodiments use "comprising" language; however, it will be understood by one of skill in the art, that in some specific instances, an embodiment can alternatively be described using the language "consisting essentially of" or "consisting of."

For purposes of better understanding the present teachings and in no way limiting the scope of the teachings, unless otherwise indicated, all numbers expressing quantities, percentages or proportions, and other numerical values used in the specification and claims, are to be understood as being modified in all instances by the term "about." Accordingly, unless indicated to the contrary, the numerical parameters set forth in the following specification and attached claims are approximations that may vary depending upon the desired properties sought to be obtained. At the very least, each numerical parameter should at least be construed in light of the number of reported significant digits and by applying ordinary rounding techniques.

Luminogen Compound of Formula (I)

The present subject matter, in one aspect, relates to a conjugated luminogen compound of formula (I) as shown in Scheme 1, below, which comprise an aggregation-induced emission (AIE) luminophore (R) and a maleimide (MI) moiety. This compound has orthogonal reactivity with thiol in the hydrothiolation or thiol-ene click reaction under mild conditions. A method for rapid, sensitive, and selective sensing of thiols conducted on solid state TLC strips is further contemplated herein.

AIE luminophores or fluorogens have been widely used in the development of bioprobe systems with high sensitivity, while selectivity remains an issue of concern. It is envisioned in the present application that introducing a functional group with an orthogonal reactivity to the AIE compound would generate an AIE fluorogen with selectivity or specificity when it is used as an AIE-active bioprobe. Maleimide (MI) is well-known for its orthogonal reactivity with thiol in the hydrothiolation or thiol-ene click reaction under mild conditions. Such designation of the MI-functionalized AIE derivatives is elaborated as follows:

Scheme 1

(I)

R = AIE compound

The AIE compound of R may be any AIE luminophore, including the following non-limiting examples of TPE derivatives and Silole derivatives. More examples of such AIE compounds are described in, for example, U.S. Application Publication No. 2010/0009362 A1, the contents of which are hereby incorporated by reference in their entirety.

wherein X and Y are, independently from each other, selected from the group consisting of alkyl, vinyl, acetyl, aryl, heteroaryl, cycloalkyl, heterocycloalkyl, and heteroalkyl. In a preferred embodiment, the AIE luminophore moiety R is tetraphenylethylene (TPE).

The luminogen compound of formula (I) may be prepared according to the synthetic procedure as presented in Scheme 2, below. The amino group in an aminated AIE derivative (AIE-AM) is transformed to the maleamic acid group in AIE-BM by reacting with maleic anhydride. Then, AIE-BM is amidated and cyclized in the presence of sodium acetate and acetic anhydride to give the desirable product of AIE-MI in a high yield.

Scheme 2

R = AIE compound

Detection of Bioanylate

Maleimide (MI) is well-known for its orthogonal reactivity with thiol in the hydrothiolation or thiol-ene click reaction under mild conditions, as shown in Scheme 3.

Scheme 3

R = AIE compound/R' = organic compound

The "clickable" nature of AIE-MI was verified by its model reaction with 1-butanethiol, which afforded the thiolated product of TPE-BSP in a yield as high as ~90% after the reaction mixture had been stirred at room temperature for a short time (2 h), as shown in Scheme 4.

Scheme 4

Figure 1:
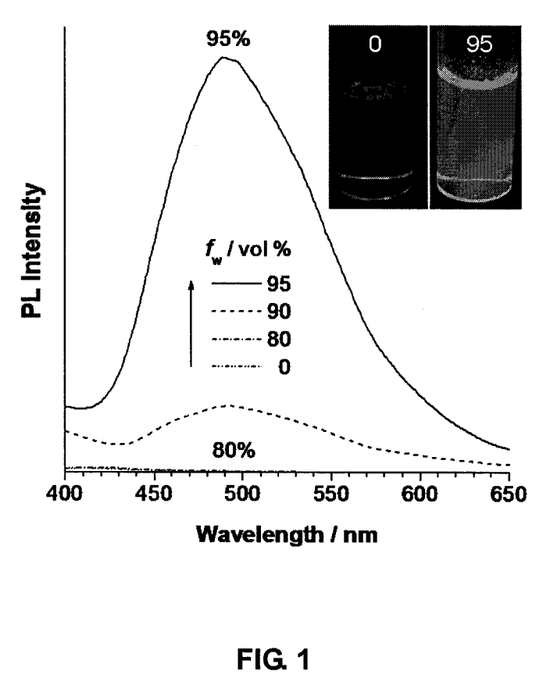
FIG. 1 shows PL (photoluminescence) spectra of TPE-AM (tetraphenylethylene-amine) in THF/water mixtures with different fractions of water ($f_w$). Inserted photos are TPE-AM was in pure THF ($f_w$=0%) and a THF/water mixture with $f_w$=95%. Photographs were taken under illumination of a 365 nm UV light.

AIE-AM is non-emissive when it is molecularly dissolved in its good solvents, such as THF, ethanol, chloroform, dichloromethane and DMSO. The PL (photoluminescence) spectrum of its dilute THF solution is basically a flat line parallel to the abscissa as shown in FIG. 1, manifesting its non-emissive nature in the solution state. However, when large amounts of water ($f_w$>80 vol %) are added into THF, intense emission spectra are recorded under identical measurement conditions. As water is a non-solvent of TPE-AM, the fluorogenic molecules must have aggregated in the aqueous mixtures with high water fractions. The PL data thus prove that TPE-AM behaves just like its parent form of TPE, that is, they are both AIE active.

Figure 2:
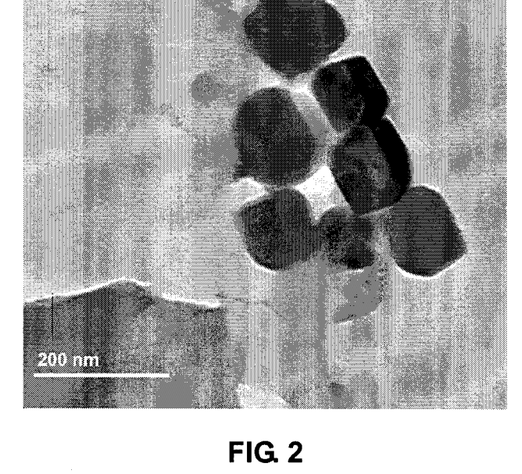
FIG. 2 shows TEM (Transmission electron microscopy) images of nanoaggregates of TPE-AM in a THF/water mixture with 95% water fraction.
Figure 3:
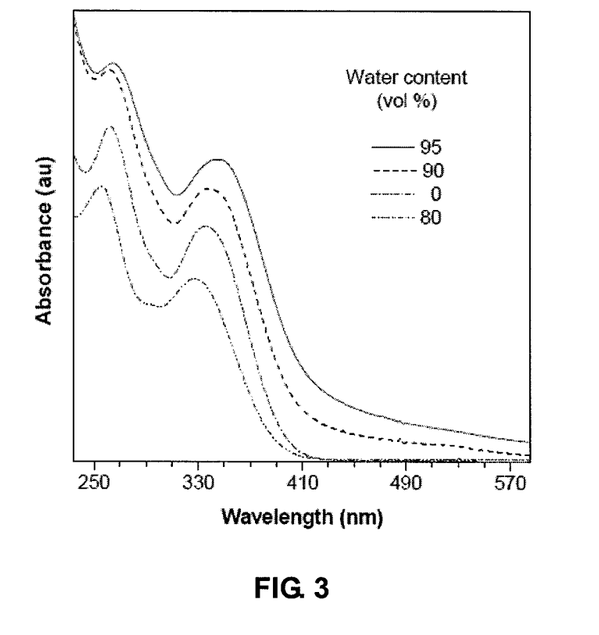
FIG. 3 shows absorption spectra of TPE-AM in THF/water mixtures with different water fractions.

The aggregates of the TPE-AM molecules are nano-dimensional in size, as proven by the embodiment of TEM images as shown in FIG. 2 and by the leveled-off tails in the long wavelength region in the absorption spectra of TPE-AM in the THF/water mixtures with high c values as shown in FIG. 3. The photographs of FIG. 3 clearly show the non-emissive and emissive nature of the molecular species and aggregative particles of TPE-AM in the THF solution and aqueous suspension, respectively. When the molecules of TPE-AM are aggregated in the THF/water mixture with 95% water, its emission intensity is increased by ~200 fold, in comparison to that of its THF solution.

Figure 4:
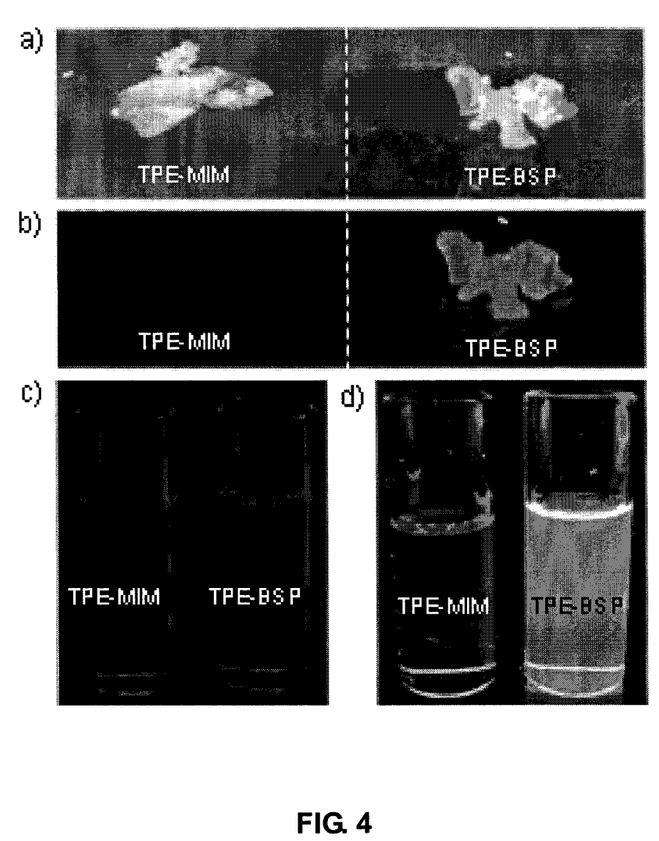
FIG. 4 shows photographs of TPE-MI (tetraphenylethylene maleimide) and TPE-BSP (a thiolated product TPE-MI with 1-butanethiol) in solid state (a and b), THF solution (c), and a THF/water mixture with 95% water fraction (d). Photographs were taken under a) normal laboratory lighting and b)-d) 365 nm UV illumination.

Whereas the nanoaggregates of TPE-AM are highly emissive, its TPE-Ml congener is non-fluorescent in either solution or solid state (FIG. 4). The fluorescence of TPE-MI is probably quenched by the exciton annihilation process associated with the n-pi electronic conjugation of the carbonyl (C=O) and olefinic (C=C) groups in its MI unit. If this is the case, breaking the n-pi conjugation should help recuperate the AIE activity. The MI unit is known to readily undergo selective electrophilic reaction with a thiol group. When a thiol group is added across the C=C double bond in the MI unit, the n-pi electronic conjugation is destroyed and the emissive ability of the dye is recovered. Thus, investigation of fluorescence behaviors of the thiolated TPE derivative, i.e., TPE-BSP, would help clarify whether the MI unit is responsible for the PL quenching in TPE-MI system.

Figure 5:
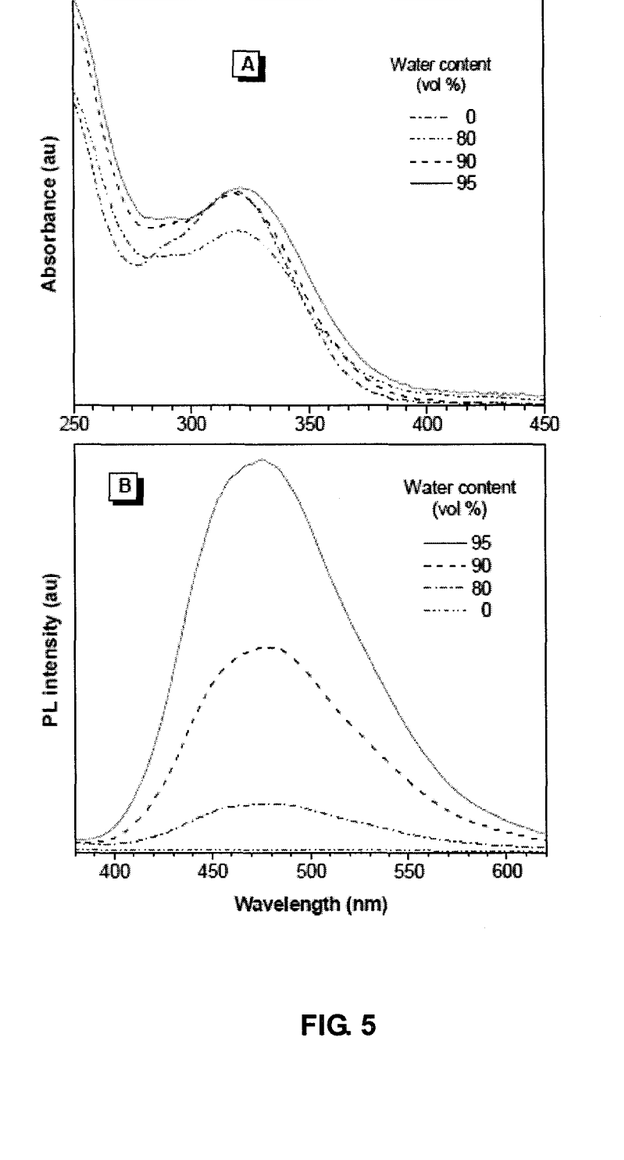
FIG. 5 shows (A) absorbance and (B) emission spectra of TPE-BSP in THF/water mixtures with different water fractions.
Figure 6:
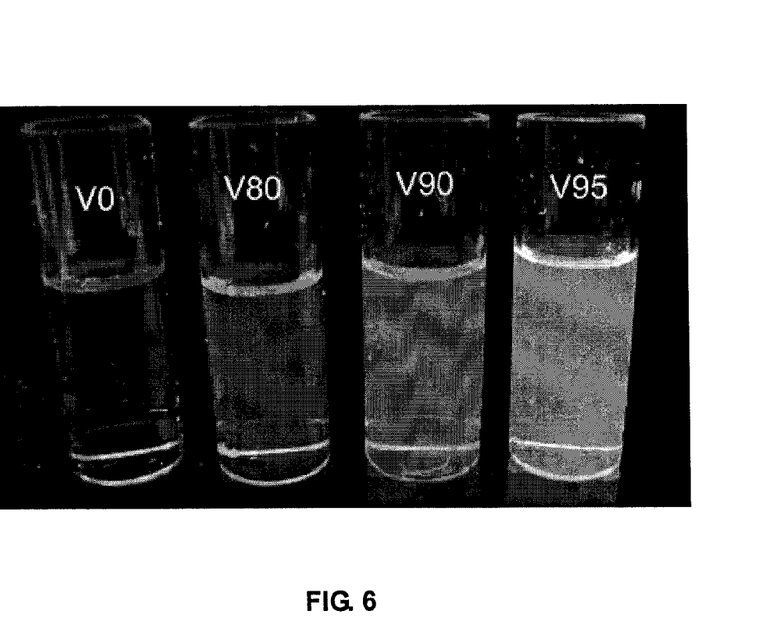
FIG. 6 shows photographs of TPE-BSP in THF/water mixtures with different water fractions taken under 365 nm UV illumination.

FIG. 4 shows TPE-MI and TPE-BSP in the solid state (see a and b), THF solution (see c), THF/water mixture with 95% water fraction (see d). Photographs were taken under normal laboratory lighting in a) and 365 nm UV illumination in b) to d). As can be seen from FIG. 4, TPE-BSP is clearly AIE active: its THF solution is non-emissive but its solid powder and aggregate suspension emit very bright sky-blue light. The UV and PL spectra as well as the photographs shown in FIG. 5 and FIG. 6 further substantiate the AIE nature of its light emission. FIG. 5 shows the absorbance spectra in (A) and the emission spectra in (B) of TPE-BSP in THF/water mixtures with different water fractions. FIG. 6 shows photogaphs of TPE-BSP in THF/water mixtures with different water fractions taken under 365 nm UV illumination.

These results are exciting, because they show that the emission of TPE-MI can be rejuvenated by its orthogonal click reaction with thiol in the aggregate state, which constitutes the foundation for the development of solid strips of fluorescent probes for thiol-specific detection.

TLC has been widely used as a handy tool in chemical research, especially for monitoring propagation of chemical transformation. Combination of TLC with spectrometric methods has led to the development of a variety of convenient analytical techniques. Accordingly, there has been much interest in expanding the usefulness of TLC and, in the work reported herein, it was tried to use TLC plates as matrix strips to develop solid-state fluorescent probes for the detection of thiol-containing biomolecules. The probe strips were prepared by dropping tiny aliquots of a TPE-MI solution in dichloromethane (~5 μM) onto the TLC plates. The plates were then dipped into DMSO solutions of the bioanalytes for 1 s. After partial evaporation of solvent, the TLC plates were examined under UV illumination.

Figure 7:
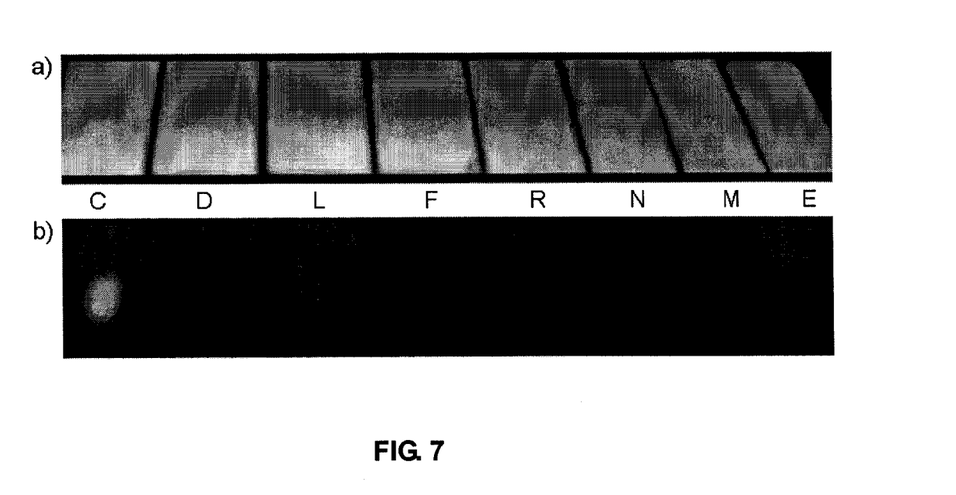
FIG. 7 shows selective detection of L-cysteine (C), a standard amino acid carrying free thiol unit, by a TPE-MI spot on a TLC (thin layer chromatograph) strip. Data for other standard amino acids containing no thiol unit, including L-aspartic acid (D), L-leucine (L), L-phenylalanine (F), L-arginine (R), L-asparagine (N), L-methionine (M), and L-glutamic acid (E), are shown for comparison. Photographs were taken under illuminations of a) 254 and b) 365 nm UV lights after the TLC plates had been dipped into DMSO solutions (0.3 mg mL$^{-1}$) of the amino acids with and without thiol unit.
Figure 8:
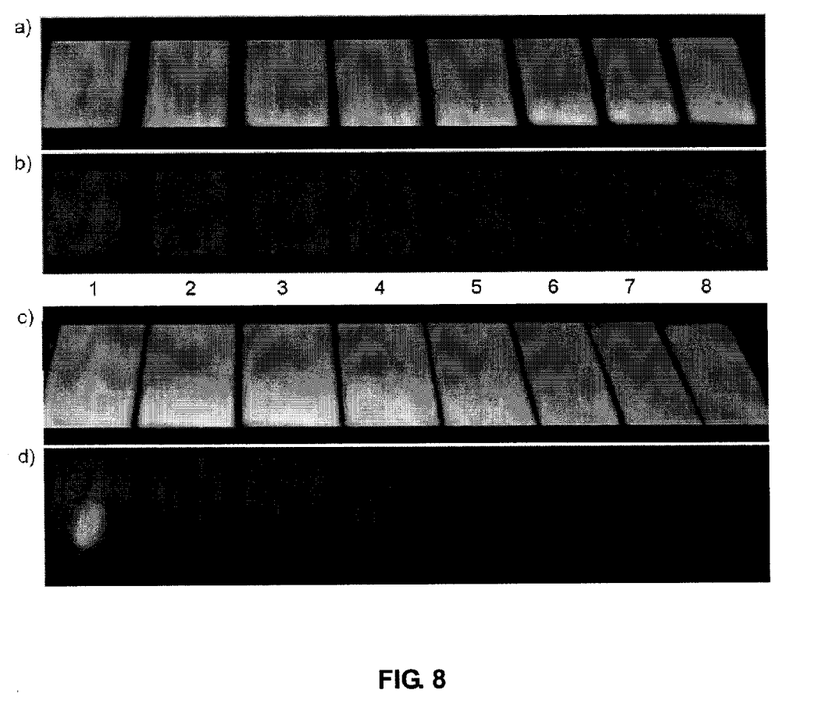
FIG. 8 shows spots of TPE-MI on TLC plates (a and b) before (c and d) and after being dipped into DMSO solutions of different amino acids: (1) L-cysteine, (2) L-aspartic acid, (3) L-leucine, (4) L-phenylalanine, (5) arginine, (6) L-asparagine, (7) L-methionine, and (8) L-glutamic acid. Photographs were taken under (a and c) 254 and (b and d) 365 nm UV light illumination.

Before dipping the TLC plates into the bioanalyte solutions, the TPE-MI spots are non-emissive under both 254- and 365-nm UV illuminations (FIG. 8, panels a and b). After being treated by the bioanalyte solutions (e.g., L-cysteine solution), the dark spot of TPE-MI on the TLC strip turns to bluish under the illumination of a 265 nm UV light (FIG. 7a). When excited by a 365 nm UV beam, the spot emits a bright blue light (FIG. 7b). In sharp contrast, the TPE-MI spots on the TLC plates treated by other amino acids containing no free thiol groups all remain non-changed in color under 254 nm UV irradiation and non-fluorescent under the 365 nm UV illumination. Evidently, TPE-Ml has readily and selectively reacted with L-cysteine to yield a fluorescent thiolated product in the solid state at room temperature. Thanks to the click nature of the involved thiol-ene hydrothiolation reaction, it does not require any heating, stirring, or catalyst, and can exhibit a response in a very short time. The detection process is fast and the assay procedure is simple. Furthermore, the contrast between the spots of TPE-MI and its thiolated product on the TLC plates is very high under the UV illumination, which is vividly discernable by the naked eyes.

Figure 9:
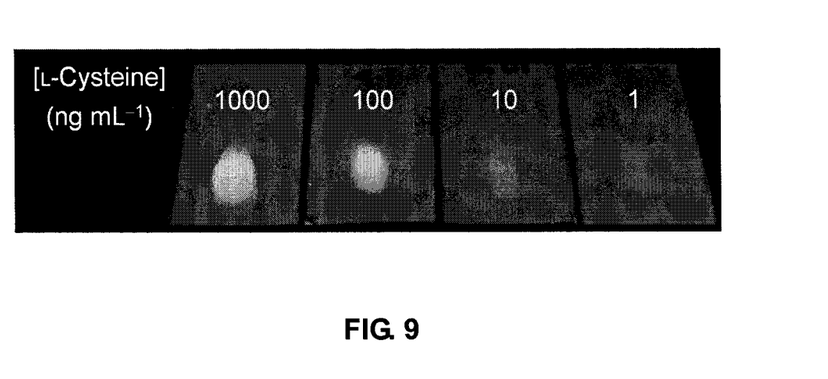
FIG. 9 shows sensitivity in fluorescent probing of L-cysteine by TPE-MI spots on TLC strips. Photographs were taken under 365 nm UV illumination after the TLC strips had been dipped into L-cysteine solutions in DMSO with concentrations of 1-1000 ng mL$^{-1}$.
Figure 10:
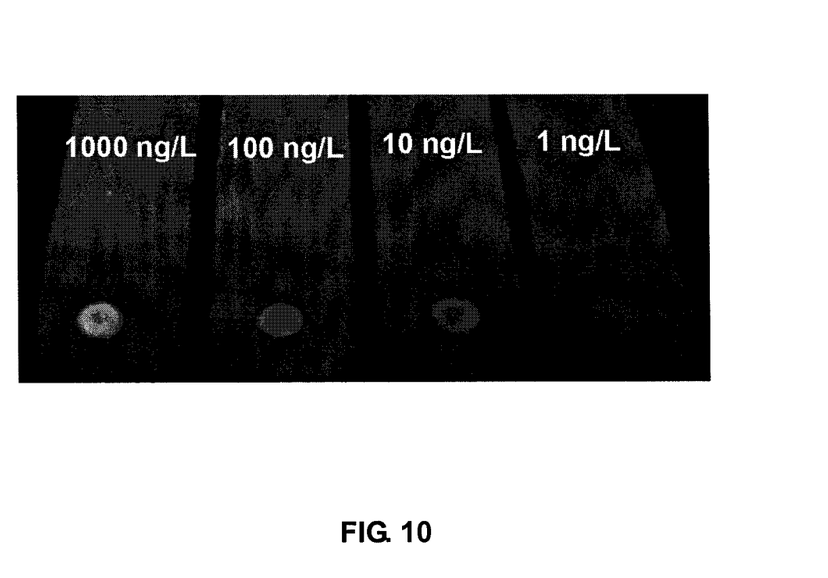
FIG. 10 shows TLC fluorescent probing of L-cysteine in DMSO solutions with different concentration using pretreated TLC plates with TPE-MI solution. Concentrations (from right to left) (ng/mL): 1000, 100, 10 and 1. Photos were taken under 365 nm UV illumination.

Selectivity and sensitivity are the two most important parameters that decide the goodness and usefulness of a bioprobe. It has become clear that the TPE-Ml probe is highly selective; it works only for free thiol. To determine how sensitive the bioprobe is, TLC detection experiments were performed using solutions of L-cysteine in different concentrations. The results are shown in FIG. 9 and FIG. 10. The TLC plate treated with a solution of L-cysteine with c=1000 ng/mL (~1 ppm) shows a spot with very bright fluorescence. Decreasing the solution concentration from 100 and 10 ng/mL lowers the emission intensity, but the spots are still clearly visible under UV illumination. Although the spot on the TLC strip treated with the 1 ng/mL (~1 ppb) solution of L-cysteine is somewhat weak, it is still discernable by the naked eye, demonstrating the high sensitivity or low detection limit of the bioprobe in the solid state.

An alternative way for assaying a trace amount of a bioanalyte is to first treat a blank TLC plate with a solution of TPE-MI and then drop an aliquot (~1 µL) of a solution of bioanalyte onto the pretreated TLC plate. FIG. 10 shows the experimental results obtained from this alternative procedure. The data are very similar to those shown in FIG. 9, once again proving the sensitive nature of the bioprobing system.

Figure 11:
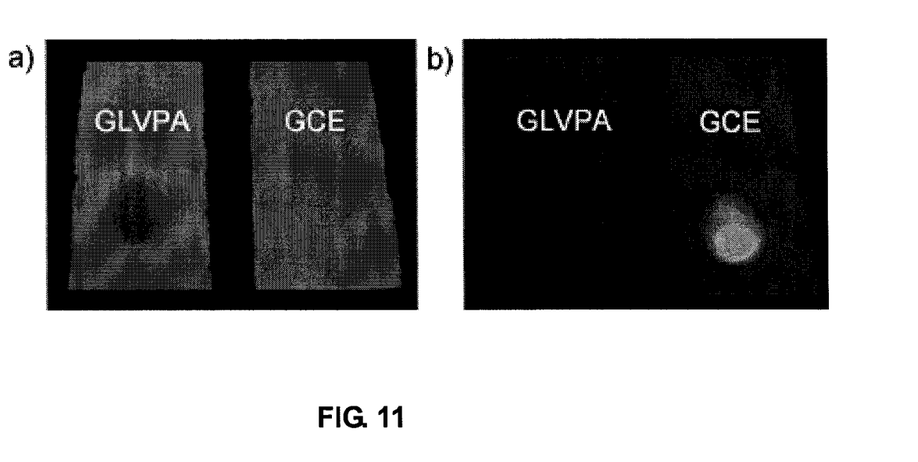
FIG. 11 shows detection of protein containing free thiol group by TPE-MI coated on TLC plate. Photographs were taken under illumination of a) 254 and b) 365 nm UV lights after the TLC plates had been dipped into DMSO solutions (0.3 mg/mL) of proteins without (GLVPA) and with thiol unit (GCE or GSH).
Figure 12:
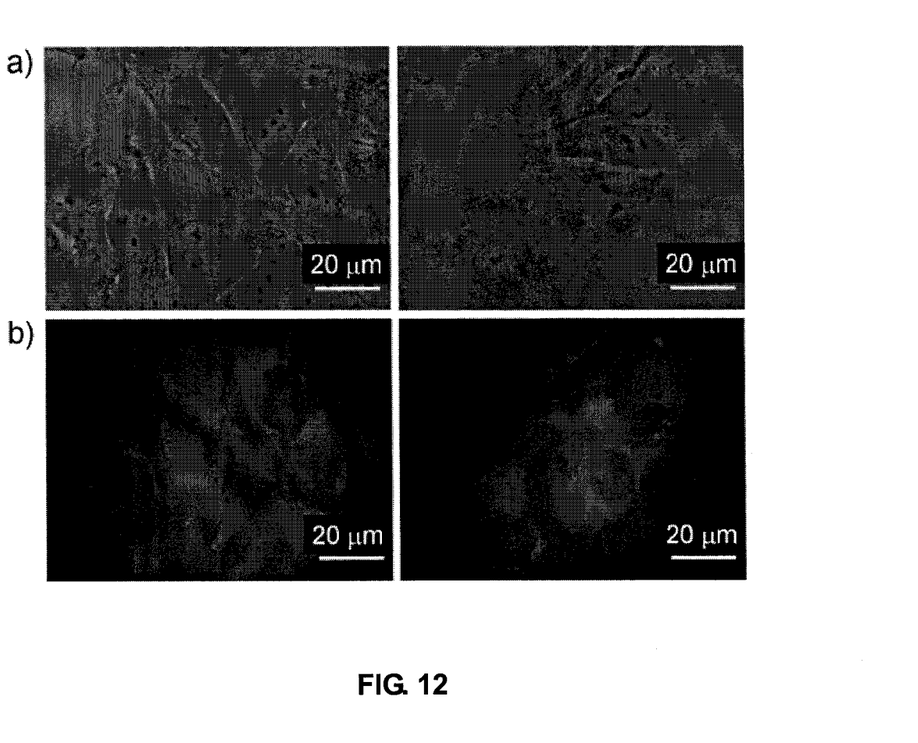
FIG. 12 shows a) bright field and b) fluorescent images of HeLa cells stained by TPE-MI nanoaggregates.

Since the free thiol group in L-cysteine can readily react with TPE-MI and selectively turn on the emission of its spot on the TLC plate in the solid state at room temperature, it was examined whether the TLC plate could be used to detect small proteins or oligopeptides containing free thiol groups under ambient conditions, in an effort to widen the applicability of the bioprobe/biosensor system. GSH (with a sequence of GCE) was used as the bioanalyte and performed the bioassay by following the experimental procedure described above. As depicted in FIG. 11, the TPE-MI spot becomes emissive after the TLC plate has been dipped into a solution of GSH with a concentration as low as about 0.3 ppm. When treated with a protein (GLVPA) that lacks free thiol group, the spot of TPE-MI remains nonemissive under UV illumination.

While the fluorescence detections of thiol-containing amino acids and proteins are of interest, monitoring thiol levels in living cells is more exciting. To explore the possibility of utilizing TPE-MI as a bioprobe for cell imaging, an attempt was made to map the thiol levels in HeLa cells using a standard cell-staining protocol. After incubating the living HeLa cells in the culture buffer in the presence of the TPE-MI nanoaggregates for 5 min, bright fluorescence images of the stained HeLa cells were recorded (FIG. 6). Closer scrutinization of the cell images reveals that the TPE-MI aggregates predominantly visualize the cytoplasmic regions. Weaker fluorescence signals are seen in the nucleus regions of the HeLa cells, which is probably due to the hydrophobic nature of the fluorogen.

The cell-imagining results show that the TPE-MI nanoaggregates can easily penetrate the cell membranes, possibly through an endocytosis process, and readily realize fluorescence labeling under the standard cell incubation conditions. All of the living cells stained by the TPE-MI nanoaggregates look healthy, indicative of good biocompatibility of the AIE fluorogen. Taking into consideration the relatively high levels of GSH in the cytosolic regions and the relationship between the cytosolic GSH levels and many health problems, this thiol-specific bioprobe may find an array of biomedicinal and biotech applications as a simple visualization tool for mapping cytosolic GSH levels in the living systems.

The bioprobe can be used in a kit for detecting the presence or absence of a thiol(s). The kit may comprise a holder and a detecting agent comprising the luminogen compound of formula (I) of claim 1, the detecting agent being held in place by the holder and being accessible to the target molecule or substance, a means for contacting the detecting agent with the sample, and a means for detecting fluorescence.

An AIE bioprobe with not only high sensitivity but also high selectivity has been described herein that utilizes a thiol-ene click reaction mechanism. Functionalization of TPE by an MI group completely quenches the fluorescence process of TPE in both solution and in the solid state. The AIE activity, however, is recovered by the orthogonal hydrothiolation reaction of the MI unit with the free thiol group in the aggregate state under ambient conditions. This unique process has enabled the development of a solid-state, thiol-specific bioprobe system based on TPE-MI spots on TLC plates. Thus, thanks to the remarkable click nature of the thiol-ene addition, the bioprobe plates selectively respond to the amino acid (L-cysteine) and protein (GSH) containing thiol groups at concentrations down to approximately 1 ppb, but not to other small and large biomolecules that lack free thiol units. The TPE-MI nanoaggregates show excellent performance as a visualization agent for mapping thiol distributions in living cells under normal cell incubation conditions. The biosensing process is simple and convenient, in addition to being highly sensitive and selective.

The present subject matter can be illustrated in further detail by the following examples. However, it should be noted that the scope of the present subject matter is not limited to the examples. They should be considered as merely being illustrative and representative for the present subject matter.

EXAMPLES

Example 1

1-(p-Aminophenyl)-2-(p-tolyly)-1,2-diphenylethylene (TPE-AM)

In a three-necked flask equipped with a magnetic stirrer were added zinc powder (3.4 g, 53 mmol) and 60 mL of THF. After the mixture was cooled to −5° C., TiCl$_4$ (2.86 mL, 26 mmol) was slowly added by a syringe. The mixture was warmed to room temperature and stirred for 0.5 h and then heated to reflux for 2.5 h. A solution of 4-methylbenzophenone (1.29 g, 6.6 mmol) and 4-aminobenzophenone (1.302 g, 6.6 mmol) in 40 mL THF was added slowly. After complete addition, the reaction mixture was heated to reflux for 12 h. After cooling to room temperature, the reaction mixture was quenched with 10% $K_2CO_3$ aqueous solution and then extracted with dichloromethane. The organic layer was collected and concentrated. The crude product was purified by silica-gel chromatography to give a light yellow solid in 40% yield (0.96 g).

$^1$HNMR (CDCl$_3$, 300 MHz), δ (TMS, ppm): 2.24 and 2.27 (two singlets, 3H), 3.57 (br, s, 2H), 6.40-6.45 (m, 2H), 6.77-6.82 (m, 2H), 6.88 (s, 2H), 6.93 (s, 2H), 6.98-7.12 (m, 10H). $^{13}$CNMR (CDCl$_3$, 100 MHz), δ(TMS, ppm): 20.94, 20.99, 114.11, 114.17, 125.77, 125.90, 127.26, 127.29, 127.31, 127.41, 128.07, 128.19, 131.00, 131.07, 131.17, 131.22, 131.24, 131.27, 132.23, 132.28, 134.1, 135.5, 139.1, 140.2, 141.0, 144.2, 144.5. MS (MALDI-TOF): m/z 362.1857 [(M+1)$^+$, calcd 362.1830].

Example 2

1-[p-(N-Maleimido)phenyl]-2-(p-tolyl)-1,2-diphenylethylene (TPE-MI)

In a 10 mL round bottom flask, a solution of TPE-AM (0.181 g, 0.5 mmol) and maleic anhydride (0.98 g, 1 mmol) in 4 mL of THF was stirred at room temperature for 12 h. After solvent evaporation, a yellow solid of TPE-BM was obtained as an intermediate, which was directly used for further reaction without isolation and purification. Anhydrous sodium acetate (0.1 g) and acetic anhydride (10 mL) were added to the flask and the mixture was stirred at 75° C. for 6 h. After cooling the solution to 0° C., TPE-MI was precipitated out. A yellow solid was isolated in 89% yield.

$^1$HNMR (CDCl$_3$, 300 MHz) δ(TMS, ppm): 2.25 and 2.26 (two singlets, 3H), 6.81 (d, 2H, J=2.4), 6.91 (d, 4H, J=4.0), 7.00-7.12 (m, 14H). $^{13}$CNMR (CDCl$_3$, 100 MHz) δ (TMS, ppm): 21.28, 21.31, 124.96, 126.55, 126.74, 127.70, 127.81, 127.88, 128.48, 128.69, 129.36, 131.30, 131.43, 132.02, 134.26, 136.32, 136.50, 139.49, 140.42, 140.63, 141.82, 143.50, 143.67, 143.87, 169.58. MS (MALDI-TOF): m/z 441.1822 [(M)$^+$, calcd 441.1729].

Example 3

3-(Butylthio)-N-[4-(1,2-diphenyl-2-p-tolylvinyl)phenyl]pyrrolidine-2,5-dione (TPE-BSP)

To a solution of TPE-MI (30 mg, 0.068 mmol) in 3 mL of dry DMSO was added 110 µL of n-butylthiol (0.147 mmol). The resultant mixture was allowed to stir for 2 h at room temperature. A large amount (100 mL) of water was then added and the solution was extracted 4 times with 20 mL dichloromethane. The organic layers were combined, dried over magnesium sulfate, and removed under reduced pressure to give TPE-BSP in 89% yield (22 mg).

$^1$HNMR (CDCl$_3$, 300 MHz) δ (TMS, ppm): 0.90-0.96 (m, 3H, CH$_3$), 1.38-1.49 (m, 2H, CH$_2$), 1.56-1.68 (m, 2H, CH$_2$), 2.25 and 2.26 (two singlets, 3H), 2.59-2.68 (m, 1H), 2.75-2.85 (m, 1H), 2.90-3.00 (m, 1H), 3.20-3.31 (m, 1H), 3.79-3.84 (m, 1H), 6.91 (d, 4H, J=7.8), 7.00-7.12 (m, 14H). $^{13}$CNMR (CDCl$_3$, 100 MHz) δ (TMS, ppm): 14.30, 21.90, 22.60, 31.70, 32.28, 36.80, 39.70, 125.99, 126.03, 127.15, 127.37, 128.28, 128.39, 128.44, 128.48, 129.05, 129.28, 130.26, 131.86, 132.00, 132.07, 132.59, 136.93, 137.14, 139.97, 140.91, 141.17, 142.57, 144.13, 144.17, 144.41, 144.91, 174.35, 176.18. MS (MALDI-TOF): m/z 531.5347 [(M)$^+$, calcd 531.2232].

Example 4

Detection of Thiols by TLC Strip

TLC probe strips were prepared by dropping tiny aliquots of a TPE-MI solution in about 5 µM of dichloromethane onto TLC plates, and the TLC plates were examined under UV illumination. The plates were then dipped into DMSO solutions of L-cystein (0.3 mg/mL) for 1 s. After partial evaporation of solvent, the TLC plates were examined under UV illumination.

The results were shown in FIGS. 7 and 8. The TPE-MI spots before dipping into the L-cystein solution, are non-emissive under both 254- and 365-nm UV illuminations (FIG. 8, panels a and b), while after being treated by the L-cysteine solution, they turned to bluish under the illumination of a 265 nm UV light (FIG. 7a). When excited by a 365 nm UV beam, the spot emitted a bright blue light (FIG. 7b). In contrast, the TPE-MI spots on the TLC plates treated by other amino acids containing no free thiol groups, i.e., L-aspartic acid (D), L-leucine (L), L-phenylalanine (F), L-arginine (R), L-asparagine (N), L-methionine (M), and L-glutamic acid (E), all remained non-changed in color under 254 nm UV irradiation and non-fluorescent under the 365 nm UV illumination (FIGS. 8 (2) to (8)).

To determine the sensitivity, the same TLC plates were dipped into the solutions of L-cysteine with different concentrations from 1000 ng/mL (~1 ppm) to 1 ng/mL (~1 ppb), i.e., four concentrations of 1, 10, 100 and 1000 ng/mL and each was examined under 365 nm UV illumination. As shown in FIG. 9 and FIG. 10, the TLC plate treated with 1000 ng/mL (~1 ppm) of L-cysteine solution showed very bright fluorescence, which was decreased in the solutions of 100 and 10 ng/mL of L-cysteine but still clearly visible under UV illumination. The TLC strip treated with the 1 ng/mL (~1 ppb) solution of L-cysteine was still discernable by the naked eye, demonstrating high sensitivity of the bioprobe of the present subject matter in the solid state.

While the foregoing written description of the present subject matter enables one of ordinary skill to make and use what is considered presently to be the best mode thereof, the person of ordinary skill will understand and appreciate the existence of variations, combinations, and equivalents of the specific embodiment, method, and examples herein. The present subject matter should therefore not be limited by the above described embodiments, methods, and examples, but by all embodiments and methods within the scope and spirit of the invention.

The invention claimed is:

1. A conjugated non-emissive luminogen compound for detecting thiols in biomolecules on solid state media, comprising an aggregation-induced emission (AIE) luminophore moiety and a maleimide moiety, represented by the following formula (I):

wherein R is an aggregation-induced emission (AIE) luminophore selected from the group consisting of:

wherein X is an unsubstituted alkyl.

2. A method of preparing the luminogen compound of claim 1 comprising reacting an aminated AIE compound with maleic anhydride, as follows:

R = AIE compound

3. A method of detecting the presence or absence of a thiol group(s) in a biological sample on solid state media comprising contacting the non-emissive luminogen compound of claim 1 with the sample, resulting in rejuvenation of fluorescence if a thiol group is present, and detecting the presence or absence of rejuvenated fluorescence.

4. The method of claim 3 comprising contacting the luminogen compound of claim 1 with free-thiol containing compounds in the sample.

5. The method of claim 3 comprising the following reaction:

wherein, R is an aggregation-induced emission (AIE) luminophore and R' is an organic substituent.

6. The method of claim 3 comprising detecting the rejuvenated fluorescence intensity by a UV-illumination reader.

7. The method of claim 3, wherein the biological sample is a biological tissue or a biological fluid.

8. The method of claim 7, wherein the biological tissue is selected from the group consisting of connective tissue, epithelium, muscle tissue, nerve tissue, organs, tumors, lymph nodes, arteries, and cells.

9. The method of claim 7, wherein the biological fluid is selected from the group consisting of urine, blood, plasma, serum, saliva, semen, stool, sputum, cerebral spinal fluid, tears, mucus and amniotic fluid.

10. A dye molecule comprising the luminogen compound of claim 1.

11. A bioprobe for detecting the presence or absence of target biomolecules on solid state media comprising a detecting agent comprising the luminogen compound of formula (I) of claim 1, the detecting agent being accessible to the target biomolecules.

12. The bioprobe of claim 11, wherein the solid state media is a TLC (Thin layer chromatography) plate or a paper-based medium.

13. The bioprobe of claim 11, wherein the biomolecules comprise a thiol group(s).

14. A kit for detecting the presence or absence of a thiol(s) in a biological sample comprising: a detecting agent comprising the luminogen compound of formula (I) of claim 1, the detecting agent being accessible to the target molecule or substance, a means for contacting the detecting agent with the sample, and a means for detecting the presence or absence of rejuvenated fluorescence.

* * * * *